(12) United States Patent
Scholz et al.

(10) Patent No.: US 9,561,134 B2
(45) Date of Patent: Feb. 7, 2017

(54) POSITIVE PRESSURE MEDICAL DRESSINGS WITH VALVE AND KITS CONTAINING SAME

(76) Inventors: Matthew T. Scholz, Woodbury, MN (US); Patricia A. Eull, Mahtomedi, MN (US); Kenneth A. Peterson, White Bear Lake, MN (US); Tony J. Kaufman, Rosemount, MN (US)

( * ) Notice: Subject to any disclaimer, the term of this patent is extended or adjusted under 35 U.S.C. 154(b) by 286 days.

(21) Appl. No.: 14/342,572

(22) PCT Filed: Aug. 31, 2012

(86) PCT No.: PCT/US2012/053302
§ 371 (c)(1),
(2), (4) Date: Mar. 4, 2014

(87) PCT Pub. No.: WO2013/039713
PCT Pub. Date: Mar. 21, 2013

(65) Prior Publication Data
US 2014/0221907 A1    Aug. 7, 2014

Related U.S. Application Data

(60) Provisional application No. 61/534,614, filed on Sep. 14, 2011.

(51) Int. Cl.
*A61F 13/00* (2006.01)
*A61F 13/02* (2006.01)

(52) U.S. Cl.
CPC ... *A61F 13/00063* (2013.01); *A61F 13/00051* (2013.01); *A61F 13/023* (2013.01); *A61F 2013/00174* (2013.01); *A61F 2013/00285* (2013.01)

(58) Field of Classification Search
CPC ............... A61F 13/00051; A61F 13/00063; A61F 13/023; A61F 13/0216; A61F 13/00068; A61F 2013/00174; A61F 2013/00285
See application file for complete search history.

(56) References Cited

U.S. PATENT DOCUMENTS

| | | |
|---|---|---|
| RE24,906 E | 12/1960 | Ulrich |
| 3,389,827 A | 6/1968 | Abere et al. |
| 3,645,835 A | 2/1972 | Hodgson |
| 3,874,387 A | 4/1975 | Barbieri |
| 4,112,213 A | 9/1978 | Waldman |
| 4,310,509 A | 1/1982 | Berglund et al. |
| 4,323,557 A | 4/1982 | Rosso et al. |

(Continued)

FOREIGN PATENT DOCUMENTS

| | | |
|---|---|---|
| EP | 0 051 935 | 5/1982 |
| WO | WO 2005/102415 | 11/2005 |

(Continued)

OTHER PUBLICATIONS

Fey, M.D. et al. "Chapter 18 -Silicone Release Coatings"; Handbook of Pressure-Sensitive Adhesive Technology; edited by D. Satas; 1982; pp. 384-403.

*Primary Examiner* — Leslie Deak
*Assistant Examiner* — Kai Weng

(57) ABSTRACT

Medical dressings and medical dressing kits that can be used to proved positive pressure wound therapy. The medical dressings include one or more normally-closed valves. The medical dressing kits may further include fittings.

18 Claims, 5 Drawing Sheets

(56) References Cited

U.S. PATENT DOCUMENTS

| | | |
|---|---|---|
| 4,472,480 A | 9/1984 | Olson |
| 4,485,809 A | 12/1984 | Dellas |
| 4,541,426 A | 9/1985 | Webster |
| 4,595,001 A | 6/1986 | Potter et al. |
| 4,598,004 A | 7/1986 | Heinecke |
| 4,600,001 A | 7/1986 | Gilman |
| 4,674,532 A | 6/1987 | Koyanagi |
| 4,737,410 A | 4/1988 | Kantner |
| 4,842,007 A | 6/1989 | Kurtz |
| 4,917,646 A | 4/1990 | Kieves |
| 5,017,254 A | 5/1991 | Noguchi |
| 5,029,579 A | 7/1991 | Trammell |
| 5,088,483 A | 2/1992 | Heinecke |
| 5,160,315 A | 11/1992 | Heinecke et al. |
| 5,188,558 A | 2/1993 | Barton |
| 5,248,275 A | 9/1993 | McGrath |
| 5,263,922 A | 11/1993 | Sova et al. |
| 5,478,310 A | 12/1995 | Dyson-Cantwell et al. |
| 5,578,022 A | 11/1996 | Scherson |
| 5,803,086 A | 9/1998 | Scholz et al. |
| 5,865,722 A | 2/1999 | Heng |
| 5,979,450 A | 11/1999 | Baker et al. |
| 6,033,426 A * | 3/2000 | Kaji .................. A61B 17/3423 600/207 |
| 6,169,224 B1 | 1/2001 | Heinecke et al. |
| 6,685,682 B1 | 2/2004 | Heinecke et al. |
| 6,742,522 B1 | 6/2004 | Baker et al. |
| D493,230 S | 7/2004 | Liedtke et al. |
| 6,867,342 B2 | 3/2005 | Johnston et al. |
| 6,893,655 B2 | 5/2005 | Flanigan et al. |
| 6,994,904 B2 | 2/2006 | Joseph et al. |
| 7,263,814 B2 | 9/2007 | Rosati |
| 7,429,687 B2 | 9/2008 | Kauth et al. |
| 7,762,045 B2 | 7/2010 | Rosati |
| 7,838,717 B2 | 11/2010 | Haggstrom |
| 7,922,116 B2 | 4/2011 | Nguyen |
| 7,955,294 B2 | 6/2011 | Stenzler |
| 2007/0156075 A1 | 7/2007 | Heinecke |
| 2008/0033377 A1 | 2/2008 | Kauth |
| 2008/0306456 A1 * | 12/2008 | Riesinger ............ A61F 13/0203 604/316 |
| 2009/0104237 A1 | 4/2009 | McGrath et al. |
| 2009/0202617 A1 | 8/2009 | Ward et al. |
| 2009/0205646 A1 * | 8/2009 | Tanaka .................. A61K 9/007 128/200.24 |
| 2011/0106030 A1 | 5/2011 | Scholz |

FOREIGN PATENT DOCUMENTS

| | | |
|---|---|---|
| WO | WO 2009/088757 | 7/2009 |
| WO | WO 2009/124100 | 10/2009 |
| WO | WO 2009/124125 | 10/2009 |
| WO | WO 2010/056544 | 5/2010 |
| WO | WO 2013/022913 | 2/2013 |
| WO | WO 2013/025955 | 2/2013 |

* cited by examiner

POSITIVE PRESSURE MEDICAL DRESSINGS WITH VALVE AND KITS CONTAINING SAME

CROSS REFERENCE TO RELATED APPLICATIONS

This application is a national stage filing under 35 U.S.C. 371 of PCT/US2012/053302, filed Aug. 31, 2012, which claims priority to U.S. Provisional Patent Application No. 61/534,614, filed Sep. 14, 2011, the disclosure of which is incorporated by reference in their entirety herein.

BACKGROUND

Hyperbaric oxygen therapy is well accepted, however, there can be serious disadvantages with systemic delivery of oxygen. Elevated systemic oxygen can result in oxygen toxicity leading to central nervous system issues, pulmonary disease, and seizures. While external hyperbaric oxygen chambers have been used over the years to treat the wounds and sores of medical patients, the following problems have persisted: (1) patient immobility and potential claustrophobia, (2) lack of portability of the equipment, (3) excessive cost for purchasing and operating specially designed oxygen delivery equipment used in conjunction with hyperbaric chambers. Many attempts have been made to simplify the therapy. For example, several have suggested using inflatable bags wrapped about limbs or even the entire lower body. These solutions are still cumbersome and do not allow patient mobility. Many others have developed compositions comprising fluids such as perfluorinated alkanes to deliver oxygen to the tissue. These compositions have questionable toxicity and wound healing potential.

There are many other medicaments that can be advantageous to wound care (e.g., antimicrobial agents, chemotaxis agents, steroids and other anti-inflammatories, growth promoters, and vasodilators), that can be delivered in a gas, vapor, or aerosolized phase under pressure. Conventional therapy requires a procedure of removing a dressing to access the wound and apply the medicament. This procedure potentially exposes the wound to contamination, can cause skin stripping, and is time consuming and costly due to frequent dressing changes. There is a need for a convenient and safe method of delivering medicaments to a wound or portion of skin without the need to remove the dressing.

SUMMARY

In one aspect, the present disclosure provides a medical dressing comprising a backing comprising an interior surface and an exterior surface; adhesive on at least a portion of the interior surface, wherein the adhesive extends around a perimeter of the interior surface of the backing to adhere the medical dressing to a subject over a wound; a normally-closed valve attached to the backing over an passage formed through the backing, wherein fluid flow through the passage is controlled by the valve, and wherein a dead volume between the normally-closed valve and the backing is 10 mm$^3$ or less; wherein, when the medical dressing is attached over the wound, the medical dressing defines a normally-sealed environment over the wound, and further wherein administration of a pressurized medicament to the external inlet of the valve opens the normally-closed valve such that fluid within the pressurized container can be administered to the normally-sealed environment, and when administration of the pressurized medicament stops, the valve is allowed to self seal.

In another aspect, the present disclosure may provide a medical dressing comprising a backing comprising an interior surface and an exterior surface; adhesive on at least a portion of the interior surface, wherein the adhesive extends around a perimeter of the interior surface of the backing to adhere the medical dressing to a subject over a wound; a normally-closed valve attached to the backing over an passage formed through the backing, wherein fluid flow through the passage is controlled by the valve, wherein the valve comprises a plurality of polymeric film layers aligned with the backing when in a closed configuration, and wherein the plurality of polymeric film layers comprises at least one flap layer comprising a flap formed therein, wherein the flap is normally sealed flat against an opposing film but opens in response to a positive pressure; wherein, when the medical dressing is attached over the wound, the medical dressing defines a normally-sealed environment over the wound, and further wherein application of a positive pressure to the external inlet of the valve opens the normally-closed valve such that fluid within a pressurized medicament container can enter the normally-sealed environment.

In some embodiments such as those provided above, the medical dressing further comprises an easy to use connection means to interface the pressurized medicament container with the valve. In one embodiment the pressurized container comprises a pressurized container with a hand operated valve to release the contents. The contents are expelled through a rigid or semi-rigid tube or straw, flexible tube, nozzle, or other connection means. In one embodiment, the connection means is easily connected to the external surface of the valve on the medical dressing by placing it through a hole in an antechamber to the valve. The antechamber may be filled with a filter including a filter capable of removing at least a portion of contaminating microorganisms.

In some other embodiments, the medical dressing further comprises an easy to use connection to interface the medical dressing with a pressurized container that is larger than a hand-held container (e.g., a gas cylinder or a house gas supply system, optionally via an outlet in a wall (or ceiling, or floor) of a room where a subject is being treated with the medical dressing), typically connected to the medical dressing by a quick-connect adapter or other means, and typically including a regulation valve to adjust the pressure of medicament that pressurizes the medical dressing. In this embodiment, the connection between the medical dressing and the pressurized container may be temporary (e.g., up to a minute, up to 10 seconds, up to 5 seconds, or even up to 1 second), or the connection between the medical dressing and the pressurized container may be more permanent (e.g., more than 1 minute, more than 10 minutes, more than 1 hour, or even more than 1 day).

The present disclosure also includes kits of any of the medical dressings of the present disclosure along with one or more containers of pressurized medicament which container is adapted to at least temporarily be connected to the medical dressing in order to deliver the medicament.

Any of the above embodiments may also comprise one or more of the following elements in any combination: a closure element, a barrier element, wound fluid absorbent material, a connection means, and a medicament reservoir.

Methods of treating a wound with the medical dressings of the present disclosure also are disclosed.

"Normally-sealed environment" refers to an environment between a medical dressing and a wound or section of intact skin over which the dressing is attached, where fluids (and solids) from the ambient atmosphere surrounding the exterior of the medical dressing cannot freely enter.

"Treatment site" refers to a wound or other portion of skin to be treated.

"Preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

As used herein, "a," "an," "the," "at least one," and "one or more" are used interchangeably. The term "and/or" means one or all of the listed elements/features or a combination of any two or more of the listed elements/features.

The above summary is not intended to describe each embodiment or every implementation of the present invention. Rather, a more complete understanding of the invention will become apparent and appreciated by reference to the following Description of Exemplary Embodiments and claims in view of the accompanying figures of the drawing.

DESCRIPTION OF EXEMPLARY EMBODIMENTS

Figure 1:
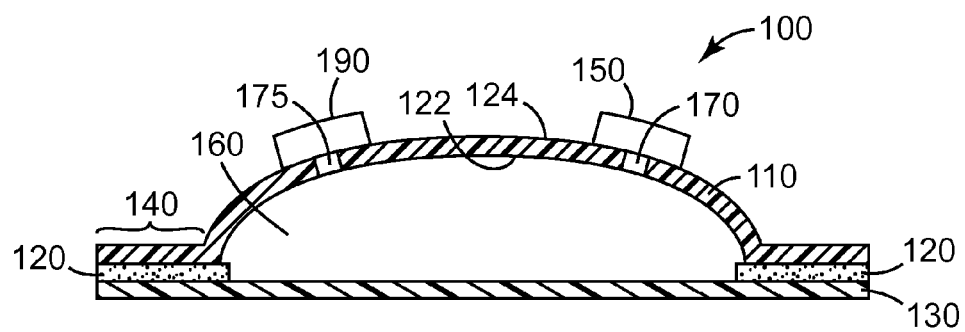
FIG. 1 is a cross-sectional view of an exemplary embodiment of a medical dressing of the present disclosure.

In the following description of exemplary embodiments of the disclosure, reference is made to the accompanying figures of the drawing which form a part hereof, and in which are shown, by way of illustration, specific embodiments in which the disclosure may be practiced. It is to be understood that other embodiments may be utilized and structural changes may be made without departing from the scope of the present disclosure.

Figure 2:
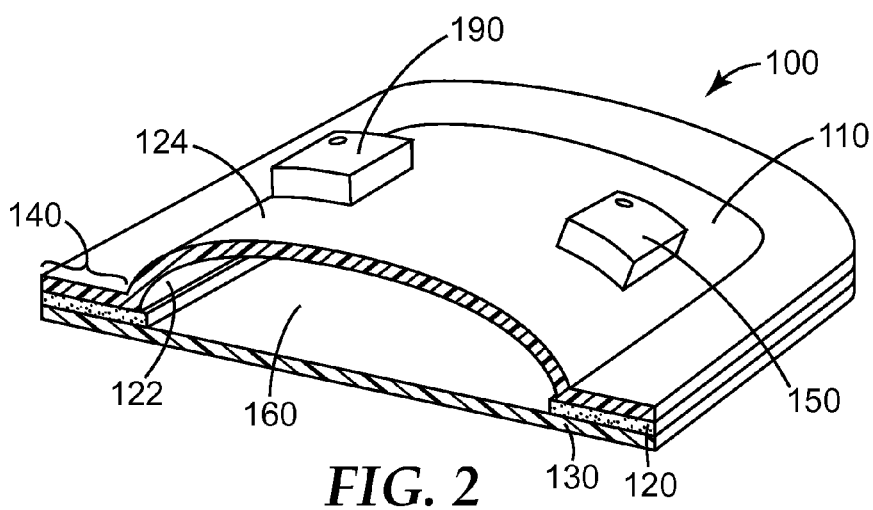
FIG. 2 is cutaway perspective view of an exemplary embodiment of a medical dressing of the present disclosure.

One exemplary embodiment of a medical dressing 100 is depicted in FIGS. 1 and 2, where FIG. 1 is a cross-sectional view the medical dressing 100, and FIG. 2 is cutaway perspective view of the medical dressing 100. Medical dressing 100 includes backing 110 (which may preferably be conformable as described herein). Backing 110 includes two opposed major surfaces: interior surface 122 and exterior surface 124. In use, interior surface 122 faces a wound (or other body site) over which the dressing is placed while exterior surface 124 faces away from the wound (or other body site).

Potentially suitable materials for backing 110 are described in more detail below, but functionally, backing 110 is preferably made of materials that serve as a barrier to bacteria, has a high moisture vapor transmission rate but is at least a temporary barrier to rapid diffusion of the medicament. The barrier properties of backing 110 may or may not be absolute. For example, backing 110 may allow for limited passage of gas, although backing 110 (and the other components of medical dressing 100) preferably provides sufficient barrier properties to the passage of the medicament such that, when placed over a wound, a positive pressure environment can be at least temporarily maintained above a wound. For example, the backing 110 may preferably have relatively high moisture vapor transmission rates, but be substantially impervious to liquids.

The medical dressings of the disclosure may be soft and conformable such that they provide a reduced likelihood of creating a pressure point that could cause wound damage if a patient were lying on the portion of the dressing for prolonged periods of time (e.g., for two hours or more).

Medical dressing 100 further includes normally-closed one-way flow control valve 150 that is affixed to backing 110 over one or more passages 170 that are formed through backing 110. Fluid flow through the one or more passages 170 in backing 110 is controlled by normally-closed one-way flow control valve 150. Normally-closed one-way flow control valve 150 (preferably, a self-sealing valve) may be used to administer a medicament under positive pressure to a wound (or intact skin area) over which dressing 100 is placed as described herein. The medical dressings of the present disclosure may include more than one normally-closed one-way flow control valve, or other additional valve(s), if additional access to the normally-sealed environment defined by the dressing is desired.

Medical dressing 100 may also include adhesive 120 on interior surface 122 such that medical dressing 100 can be adhered to a subject over a wound with interior surface 122 facing a wound. Adhesive 120 may cover all or part of interior surface 122 in a continuous, discontinuous, and/or pattern coated fashion. Adhesive 120 in FIGS. 1 and 2 is depicted only around perimeter 140 of the dressing. In other embodiments the adhesive covers interior surface 122 more completely, or even completely. Importantly, in many embodiments adhesive 120 seals dressing 100 to the skin preventing rapid escape of the medicament administered. In addition, adhesive 120 may include one or more adhesives. Adhesive 120 may contain an optional medicament in the adhesive or on the surface of the adhesive.

Adhesive 120 in the exemplary embodiment depicted in FIG. 1 is provided only around perimeter (i.e., border) 140 of backing 110 such that adhesive 120 forms a frame around a central part of interior surface 122 of backing 110. One arrangement places dressing 100 over a wound while adhesive 120 is attached to the tissue (e.g., skin) surrounding the wound or skin location. Medical dressing 100, along with the wound and the tissue surrounding the wound, preferably define a normally-sealed environment in which the wound is isolated from the surrounding environment. Once the medicament is administered the backing may inflate. Medical dressing 100 in FIGS. 1 and 2 is shown in an inflated condition. Interior surface 122 of backing 110 faces the normally-sealed environment in which the wound is located while exterior surface 124 of backing 110 faces away from the wound.

Adhesive 120 may preferably be exposed on only a portion of interior surface 122 of backing 110. In the embodiment depicted in FIGS. 1 and 2, adhesive 120 is provided on only a portion of interior surface 122 (i.e., the central portion of interior surface 122 is free of adhesive 120). In other embodiments, however, adhesive may be provided over substantially all of interior surface 122 with a portion of the adhesive covered by another element such that only a portion of the adhesive remains exposed for attachment to a subject.

In any embodiment, however, it may be preferred that adhesive 120 extend continuously around perimeter 140 of backing 110 such that medical dressing 100, when attached to a subject, can form a normally-sealed environment over a wound, with the bounds of the normally-sealed environment being defined by interior surface 122 of backing 110 as adhered to the subject over a wound or skin site by adhesive 120.

As shown in FIGS. 1 and 2, medical dressing 100 is typically provided with release liner 130 to protect adhesive 120 prior to application over a wound. Release liner 130 is typically removed prior to application of medical dressing 100 over a wound.

Referring again to FIGS. 1 and 2, with the use of a suitable normally-closed one-way flow control valve 150, the normally-sealed environment created by a dressing 100 attached over a wound may preferably be maintained at a positive pressure (i.e., pressure above the ambient atmospheric pressure on exterior surface 124 of backing 110). The positive pressure is often referred to as the gauge pressure. Suitable gauge pressure would be just enough to inflate the dressing or dressing reservoir. The positive pressure may range from 0.01 mmHg to 700 mmHg. Typically the inflated pressure immediately after inflation is at least 0.1 mmHg, preferably as least 1 mmHg. The upper limit is determined by the integrity of the dressing seal and/or the materials used to construct the dressing and any reservoir present. The pressure should not be so high that the dressing seal is compromised or that excessive pressure is placed on the wound which may delay wound healing.

Typically, the inflation pressure will not exceed 500 mmHg and may not exceed 400 mmHg or even 200 mmHg or even 100 mmHg. In some embodiments a highly porous spacer may be placed in the reservoir to maintain the reservoir volume. In this design a positive pressure within the reservoir may not be necessary. Thus, the medicament may be placed in the chamber but not in a pressurized condition, i.e. the pressure within the reservoir is essentially the same as that of the exterior ambient condition. Suitable spacers include highly porous materials such as nonwovens, foams, particle networks, and the like. In this embodiment it may be beneficial to include an exit valve that opens to allow the medicament to be flushed through the cavity. The exit valve like the inlet valve is preferably low profile and flexible and may be self sealing. Alternatively, the exit port may be simply an adhesive tab covering an opening which is opened when filling the medicament reservoir.

Another method of filling an ambient pressure reservoir with resilient spacer would be to provide the dressing in a compressed state that can be inflated with the medicament.

It may be preferred that the valves be capable of being used one, two or more times to administer gaseous and/or aerosol medicament fluids to the normally-sealed environment and/or reservoir. For example, fluid can be administered to the normally-sealed environment through the valve as described herein, with the valve opening by communicating with the pressurized medicament source and being allowed to close when the pressurized medicament administration terminates. As the positive pressure (inflation) deteriorates, it can be simply re-inflated through the valve as described herein.

In some embodiments, the medical dressing includes absorbent material to absorb fluids (e.g., liquids) entering the normally-sealed environment. Examples of potentially suitable absorbent materials may include hydrocolloids, hydrogels, hydrophilic foams, woven materials, nonwoven materials, absorbent fiber fabrics, absorbent films, and combinations thereof. The absorbent material may be both absorbent and capable of releasing any optional medicament contained therein which may be the same or different from that administered under pressure.

Kits also are possible where a wound absorbent or contact layer is placed over or in the wound followed by application of the dressing and finally inflation with the medicament.

Although the magnitude of the positive pressure maintained in the normally-sealed environment by dressing 100 will typically deteriorate over time (after reaching a maximum during administration of medicament fluids to the normally-sealed environment and/or reservoir through normally-closed one-way flow control valve 150), it may be preferred that medical dressing 100 be capable of maintaining the positive pressure for at least some significant period of time. In some embodiments, it may be preferred that medical dressing 100 be capable of maintaining at least some level of positive pressure in the normally-sealed environment (in the absence of active vacuum source) for a period of 1 minute or more, 5 minutes or more, 10 minutes or more, 15 minutes or more, 30 minutes or more, or even 60 minutes or more.

In some embodiments, normally-closed one-way flow control valve 150 is formed from multiple film layers such as those described in U.S. Pat. Nos. 4,674,532, 4,917,646, 5,017,254, and 5,188,558. Another type of normally-closed one-way flow control valve is described in U.S. Pat. No. 4,842,007. These patents are incorporated herein by reference. A particularly preferred normally-closed one-way flow control valve is that incorporated into ANAGRAM MYLAR 18 INCH DIAMETER BALLOONS (Anagram International, Inc., a division of Amscan, Inc., Eden Prairie, Minn.). Self sealing flat valves of this type are disclosed in U.S. Pat. Nos. 5,378,299 and 5,248,275.

The base layer of normally-closed one-way flow control valve 150 may be attached to the backing 110 by any suitable technique or combination of techniques (e.g., adhesives, heat sealing, chemical welding, thermal welding, ultrasonic welding). In a one embodiment, backing 110 serves as the base layer of normally-closed one-way flow control valve 150. In a another embodiment normally-closed one-way flow control valve 150 is formed as a separate component, including a base layer, and the base layer of the valve is attached to backing 110 by a suitable adhesive or heat seal.

Transformation of normally-closed one-way flow control valve 150 between the open and closed configurations may be performed selectively, although it may be that normally-closed one-way flow control valve 150 is normally closed such that, in the absence of an applied external force capable of opening normally-closed one-way flow control valve 150, normally-closed one-way flow control valve 150 is closed.

The valves may be self-sealing and inflation of the chamber results in a force that may assist in closing the valve. In some embodiments, normally-closed one-way flow control valve 150 may be opened by a pressure differential placed across the valve. For example, normally-closed one-way flow control valve 150 may be opened when the fluid medicament pressure on the side of normally-closed one-way flow control valve 150 facing in the same direction as exterior surface 124 is sufficiently larger than the forces operating on the valve to retain it in the closed configuration. The pressure differential at which the valve moves from the closed configuration to the open configuration may be referred to as the "cracking pressure". The cracking pressure of these self-sealing valves may be a function of the inflation pressure. The cracking pressure will be greater than the internal inflation pressure.

The pressure differential across the valve may be achieved by connecting a pressurized medicament source. For example, the medicament source may be a can of pressurized oxygen. For example, Just Oxygen (Oxygen Bar Party, Los Alamitos Calif.) is a small can of oxygen that delivers a total of 8 liters of pure oxygen. This would be sufficient to inflate and re-inflate a dressing multiple times. The valve on the pressurized medicament container may have a straw as is common on spray lubricants such as WD-40 (WD-40 Company, San Diego, Calif.). Alternatively, the valve on the pressurized container may have a fixed means of easily communicating with and delivering the medicament through the valve.

Medical dressing 100 can include optional exit valve 190 over optional exit passage 175 defined through backing 110, wherein optional exit valve 190 is normally closed, but under pressurization from interior space 160 optional exit valve 190 can open to permit fluid to be withdrawn from medical dressing 100 through optional exit passage 175. Optional exit valve 190 is preferably a one way out valve such as those described in U.S. Patent Application Publication No. US2011/0106030, which is incorporated by reference herein for this purpose.

Figure 3A:
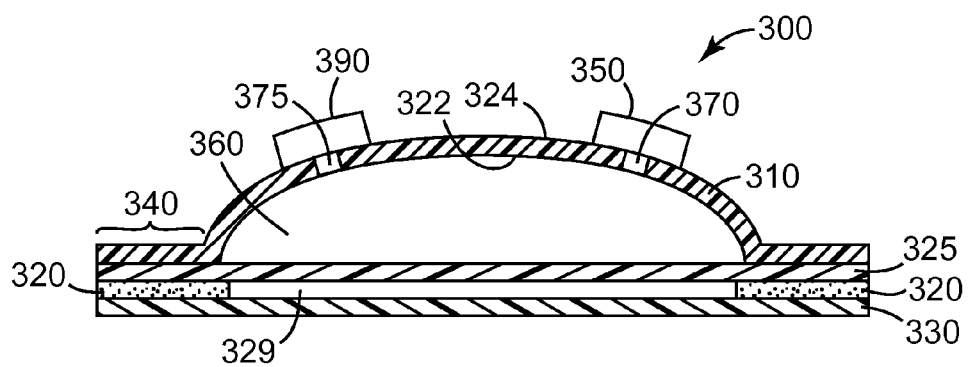
FIGS. 3A, 3B, and 3C are cross-sectional views of exemplary embodiments of medical dressings of the present disclosure.

FIG. 3A shows an embodiment of medical dressing 300, which resembles medical dressing 100, having backing 310 with interior surface 322 opposing exterior surface 324, normally-closed one-way flow control valve 350 affixed to backing 310 over one or more passages 370, perimeter 340, adhesive 320, optional liner 330, and optional exit valve 390 (over optional exit passage 375), but further comprises film layer 325 affixed to perimeter 340 of backing 310, forming a reservoir (or "pocket") 360 between film layer 325 and backing 310. Reservoir 360 so formed can be filled with a medicament through normally-closed one-way flow control valve 350 affixed to backing 310. Importantly, film layer 325 is permeable to the medicament. For example, when the medicament is oxygen the film layer 325 (and any adhesive which may be present) should be permeable to the medicament (oxygen). While reservoir 360 appears as a single compartment it may be segregated into multiple smaller compartments in communication in order to minimize expansion or "pillowing" of the dressing after inflation.

Suitable oxygen permeable films for film layer 325 include thermoplastic polymers, thermoset polymers and laminates thereof. Both thermoplastic and thermoset films may optionally contain fillers, plasticizers, tackifiers and other additives which may alter the permeability. Suitable films include polyurethanes, polyolefins including polyethylene and polypropylene, modified celluloses such as cellulose esters including but not limited to cellulose acetate, polyacrylates, aromatic and aliphatic polyesters (e.g., PET, PETG, polylactic acid, polybutylene terephthalate), silicones, block copolymers (e.g., SIS, SBS) and those available from Kraton Polymers Inc., polyvinylidene chloride, fluorinated polymer films including polytetrafluorethylene (Teflon) and poly(chlorotrifluoro)ethylene (Kel F). It is understood that film layer 325 also may be a microporous film to allow very rapid transport of the medicament. The pores of the microporous film may or may not be filled with a second polymer. Aerosol medicaments may require film layer 325 to be a microporous membrane in order to have sufficient diffusion rate. Suitable microporous membranes include gas-permeable but liquid-resistant microporous membranes which may be formed by a number of different processes including solvent casting, thermally induced phase separation, exposing the membrane to radiation that weakens the plastic and creates specific areas that can be removed by dousing the membrane in acid (or other chemicals), stretching or expanding films and the like. Supporting nonwovens or other fabrics may be attached to the membrane to provide support. In one embodiment, the microporous material is an expanded PTFE material having a polyester, polyethylene or polypropylene mesh support which facilitates attachment.

In some embodiments, film layer 325 is molecularly permeable to the medicament. In some embodiments, the permeability may be used to control the rate of delivery. For example, in the case of the use of oxygen as a medicament film layer 325 is permeable to oxygen but remains impermeable to other materials (e.g., wound fluids, bacteria, or virus) and is highly permeable to allow rapid delivery of the oxygen. In the case of nitric oxide (NO), the gas delivered is a dilute solution of NO and film layer 325 may be slightly permeable to NO to control the rate of delivery.

Note that in certain embodiments it may be desirable to administer more than one medicament to a treatment site. This can be done by incorporating multiple reservoirs to which medicaments may be administered, administering said medicaments to a single reservoir or dressing, or administering one or more medicaments to the reservoir and one or more medicaments to the normally-sealed treatment site. Thus, each reservoir would have a valve through which a medicament can be administered and the dressing may optionally comprise a valve communicating directly to the normally-sealed treatment site. While shown as a single reservoir 360 in FIG. 3A, it is understood that one, two, three or more reservoirs may be present. The films or membranes of film layer 325 may be treated on one or both sides to make the film hydrophobic or hydrophilic. For example, to transport an aqueous aerosolized medicament through the film layer 325 it may be advantageous to provide a hydrophilic film that is easily wetted by the aqueous phase of the aerosol.

Note that FIG. 3A has depicted reservoir 360 above film layer 325. Alternatively, or additionally, an inflatable reservoir may be placed beneath film layer 325, in optional region 329.

Figure 3B:
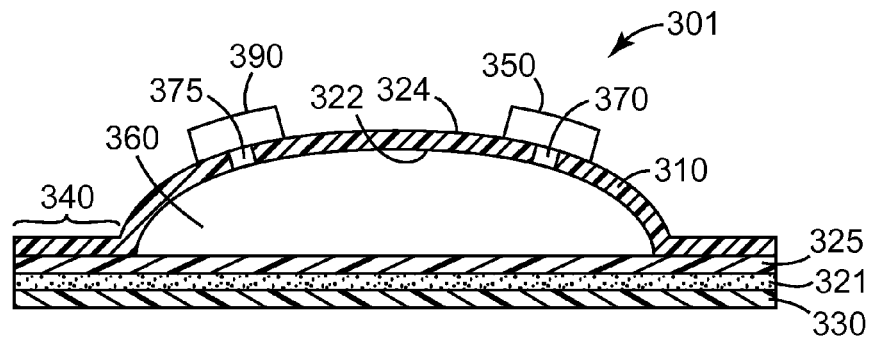

FIG. 3B is a cross-sectional view of an exemplary embodiment of medical dressing 301 of the present disclosure, similar to medical dressing 300 except that adhesive 321 is provided on film layer 325, covering all or part of film layer 325 in a continuous and/or patterned fashion.

Figure 3C:
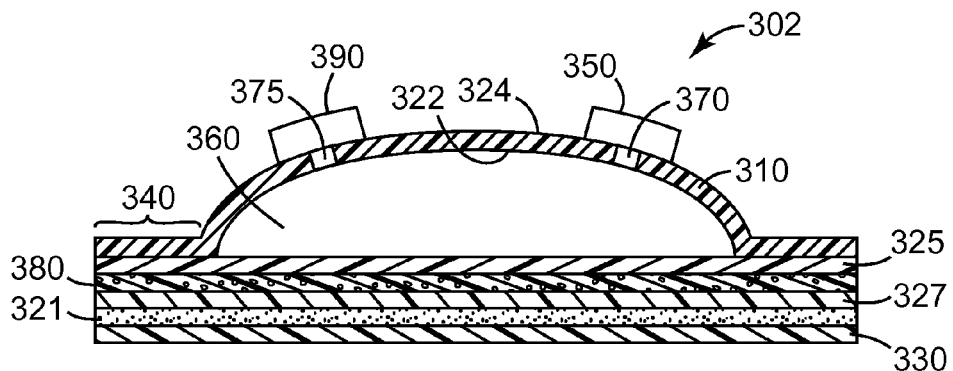

FIG. 3C is an exemplary embodiment of medical dressing 302, similar to medical dressing 301 but including absorbent layer 380 between film layer 325 and adhesive layer 321. Optional film layer 327 is also shown in FIG. 3C, which can be useful in embodiments where absorbent layer 380 is beneficially held in place. In some embodiments, absorbent layer 380 has sufficient structural integrity (e.g., as in the case of some foams) so that optional film layer 327 may not be required. If optional film layer 327 is included, it should be permeable to the medicament, as described for film layer 325.

Normally-closed one-way flow control valve 150 (or 350) used in the medical dressings of the disclosure may be soft and conformable such that it provides reduced likelihood of creating a pressure point that could cause wound damage if a patient were lying on the portion of the dressing containing the valve for prolonged periods of time (e.g., for two hours or more). The normally-closed one-way flow control valves may be so conformable that the valve, even as attached to the dressing, can be manually folded over between the thumb and the forefinger of a person such as a healthcare worker in at least one direction and preferably in multiple directions. Normally-closed one-way flow control valves may recover fully from folding. In some embodiments, normally-closed one-way flow control valves are drapable (i.e., they bend over under their own weight). Drapable valves comprise a laminate of at least two film layers.

Figure 4:
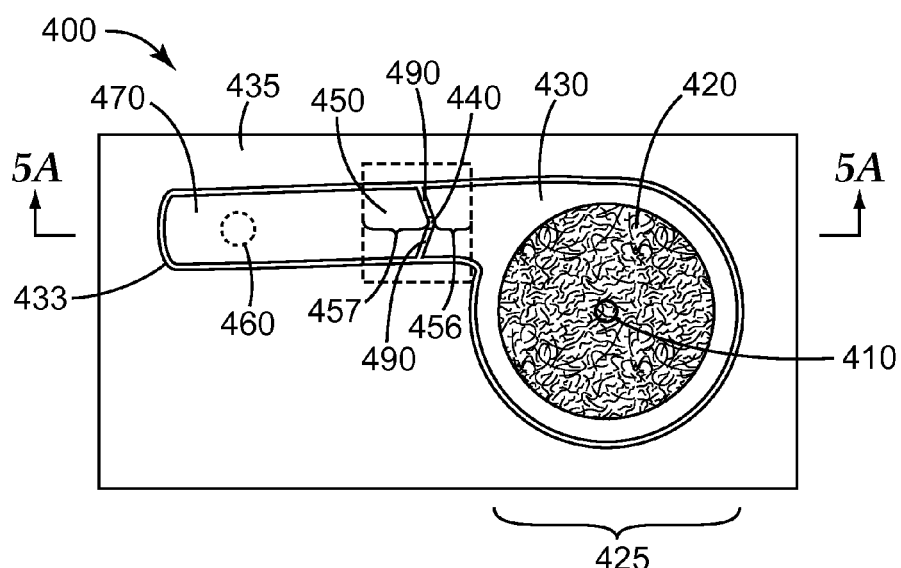
FIG. 4 is a schematic plan view of an exemplary embodiment of a normally-closed one-way flow control valve of the present disclosure.

FIG. 4 shows an exemplary embodiment of a normally-closed one-way flow control valve 400 having valve reed 450 that defines valve inlet 440, antechamber 425 that defines instillation port 410, and exit chamber 470 that defines valve outlet 460. Valve reed 450 communicates with antechamber 425 through valve inlet 440, and valve reed 450 is typically in fluid communication with interior surface 122 of medical dressing 100 through valve outlet 460, which is typically aligned with one or more passages 170 in backing 110. Valve reed 450 has, in addition to valve inlet 440, antechamber reed portion 456 and exit chamber reed portion 457. A bond is provided along perimeter bond 433 that bonds together the several layers of the normally-closed one-way flow control valve (e.g., by ultrasonic welding or heat-sealing), as is evident in the cross-sectional views in FIGS. 5A and 5B (taken along "5A" in FIG. 4). Transverse bonds 490 and 491 provide additional bonding of the several layers of the normally-closed one-way flow control valve. It will be noted that valve reed 450 is not bonded together at valve inlet 440. During a bonding process to provide transverse bonds 490 and 491, a temporary spacer element (not shown) may be provided in valve inlet 440, to keep valve inlet 440 from being bonded closed, and subsequently the temporary spacer element (not shown) is removed from valve inlet 440. Optionally, normally-closed one-way flow control valve 400 includes a film portion 435 surrounding all or part of the perimeter bond 433.

Antechamber 425 may have a height of 2-20 mm or more. Antechamber 425 serves to provide a visual queue to where the medicament should be instilled and may facilitate installation of normally-closed one-way flow control valve 400. Medicament is instilled through instillation port 410. Optionally, support material 420 (a foam, nonwoven or other resilient porous material) is provided, and in some embodiments support material 420 serves to keep the antechamber 425 open to facilitate insertion of, for example, an inflation tube or straw.

Antechamber 425 is in fluid communication with valve reed 450 to facilitate delivery of the medicament. For example, antechamber 425 may include a resilient foam filled bulb 430 comprising an elastomeric film and defining instillation port 410. In some embodiments, instillation port 410 is designed to be slightly smaller in diameter than a straw or inflation tube through which medicament passes from a pressurized container. When the straw or inflation tube is placed through instillation port 410 into antechamber 425, the elastomeric film of resilient foam filled bulb 430 seals around the straw, providing a seal.

Figure 5A:
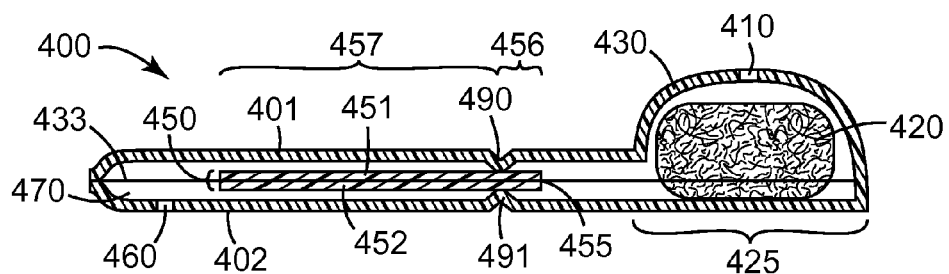
FIGS. 5A and 5B are cross-sectional views of an exemplary embodiment of a normally-closed one-way flow control valve of the present disclosure.

FIG. 5A is a cross-sectional view (taken along "5A" in FIG. 4) of an exemplary embodiment of normally-closed one-way flow control valve 400. Normally-closed one-way flow control valve 400 includes film layers 401 and 402 bonded (e.g., by ultrasonic welding or heat-sealing) along peripheral bond 433, enclosing valve reed 450 as well as optional support material 420. In some embodiments, film layer 402 can optionally be part of the dressing construction (e.g., a portion of backing 110 can serve as the "base layer" of normally-closed one-way flow control valve 400).

Valve reed 450 can be formed, for example, by ultrasonic welding or heat-sealing a perimeter of two valve reed film layers 451 and 452 (e.g., along the portions of 450 that lies along perimeter bond 433 and transverse bonds 490 in FIG. 4), excepting that portion of the perimeter where valve inlet 440 exists. It will be noted that valve reed film layers 451 and 452 are not bonded together at valve inlet 440, and also are not bonded together at those portions that do not lie along any perimeter bonds, to allow for fluid communication between antechamber 425 and exit chamber 470. Preferably, valve reed film layers 451 and 452 are flexible and flat to ensure that valve reed film layers 451 and 452 reversibly "seal" together to permit retention of medicament in medical dressings of the present disclosure, but do not excessively "block" together (i.e., bond tightly enough to resist instillation of pressurized medicament), which may cause the valve not to open.

Figure 5B:
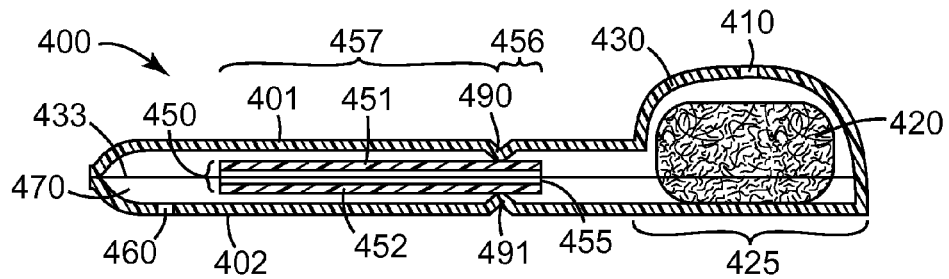

In FIG. 5A, valve reed 450 is shown with valve reed film layers 451 and 452 in contact with each other (i.e., valve reed passage 455 is in a "sealed" condition). In FIG. 5B, valve reed film layers 451 and 452 are shown parted (i.e., valve reed passage 455 is in an "open" condition), as would occur during instillation of the medicament from pressurized container (not shown).

As discussed herein, it may be preferred that the profile or height of the valves be limited to improve patient comfort and increase resistance to displacement by external forces (e.g., from bedding or clothing). For example, the preferred valves are virtually undetected when a patient lies on them when sleeping on a mattress. The low profile valves may also improve patient comfort where, for example, the medical dressing is placed in a location on which the patient's weight rests while sitting, lying, and/or standing.

One manner in which the low-profile valves used in connection with the medical dressings can be characterized may be in terms of maximum of the valve structure as measured normal to the major surfaces of the backing (where the major surfaces of the backing are the interior surface and the exterior surface). It may be preferred, for example, that the valves used in the medical dressings have a maximum thickness (not including optional resilient foam filled bulb 430) of 3 millimeters or less, in some embodiments 2 millimeters or less, or even 1 millimeter or less, and more preferably 0.5 millimeter or less (e.g., even 200 micrometers or less) in a non-pressurized condition on a flat surface. Films used to make these valves typically have a thickness less than 250 micrometers, preferably less than 150 micrometers, more preferably less than 125 micrometers. The films used to make the valves typically have a thickness of at least 25 micrometers and preferably at least 50 micrometers.

Another manner in which the low-profile valves can be characterized may be in the form of dead volume between the normally-closed valve and the backing. As used herein, the term "dead volume" refers to the volume or space in which fluids may accumulate between the valve and the interior surface of the backing when the valve is in its normally-closed configuration (i.e., that volume or space within exit chamber 470 in FIG. 5A). Reducing the dead volume between the normally-closed valve and the interior surface of the backing can help to reduce the profile of the valve and the dressing as a whole.

The dead volume defined by a normally-closed valve and backing in a medical dressing of the present disclosure may preferably be 10 cubic millimeters ($mm^3$) or less, in some embodiments 6 $mm^3$ or less, or even 4 $mm^3$ or less, and further, in some embodiments, even 2 $mm^3$ or less (e.g., 1 $mm^3$ or less). In the some embodiments the valves are designed to have essentially no dead volume since they form a film/film seal. It is understood that some very small dead volume will exist but it is less than about 0.2 $mm^3$. Dead volume is measured with the valve in a relaxed state with no inflation in the dressing.

The valve may be incorporated into a port or tubing connection, however, elastomeric tubing can form a relatively rigid structures can cause pressure points when the patient is lying on the wound, for example, when in bed. Thus, if tubing is used it should be soft and relatively easy to collapse in order to prevent pressure point formation. So called "lay-flat" tubing with a valve may be used. In a tubing valve a duck bill check valve may be used that is a one way valve allowing medicament into the dressing but not allowing the pressurized gas or aerosol to escape. Suitable examples of duck bill check valves include those available from Vernay Laboratories, Inc. (Yellow Springs, Ohio).

Another optional element that may be included with the medical dressings are filter elements that may be placed proximate the valve(s) of the medical dressings or on the medicament delivery container or both. The filter elements may function to filter materials which may be present in the medicament container (e.g., bacteria, virus, or spores) which should not enter the normally-sealed environments defined by the medical dressings. The filter elements may be provided attached to the medical dressings proximate the exterior valve surfaces of the backings of the medical dressings. For example, as shown in FIG. 4, support material 420 within antechamber 425 can function to filter the inbound medicament. The filter elements may be provided using a variety of different materials. Examples of some potentially suitable materials for the filter elements may include fabrics (e.g., gauze, nonwoven fabrics, woven fabrics, knitted fabrics), foams, porous membranes, and laminates thereof.

Figure 6:
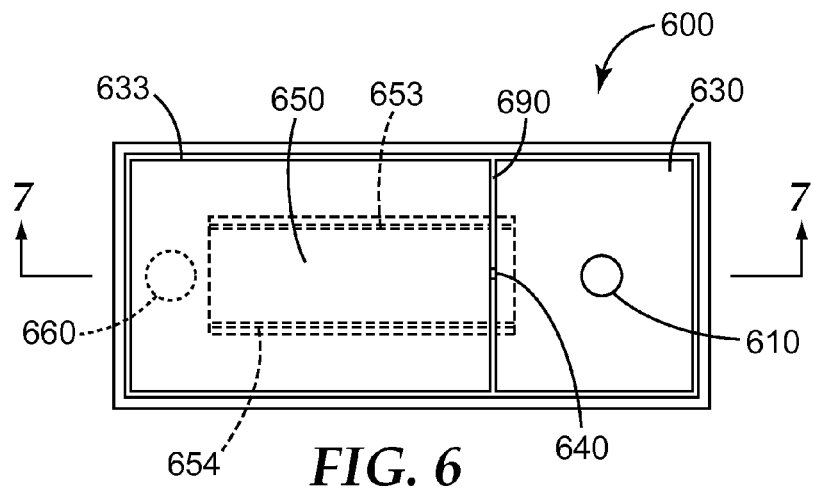
FIG. 6 is a schematic plan view of an exemplary embodiment of a normally-closed one-way flow control valve of the present disclosure.

FIG. 6 shows an exemplary embodiment of a flat film normally-closed one-way flow control valve 600 having valve reed 650 extending from antechamber 630 through valve inlet 640 to exit chamber 670. Valve reed 650 is a flat tube. Valve reed 650 can be formed, for example, by ultrasonic welding or heat-sealing together two pieces of flat film along valve reed edges 653 and 654. Preferably, the film used for valve reed 650 is flexible and flat to ensure that layers reversibly "seal", but do not excessively "block" together, which may cause the valve reed not to open.

Figure 7:
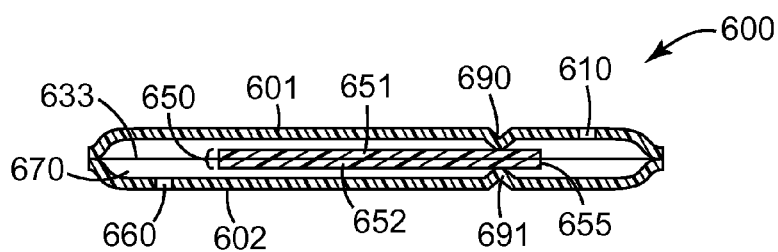
FIG. 7 is a schematic cross-sectional view of an exemplary embodiment of a normally-closed one-way flow control valve of the present disclosure.

FIG. 7 is a cross-sectional view (taken along "7" in FIG. 6) of normally-closed one-way flow control valve 600. Normally-closed one-way flow control valve 600 includes upper and lower film layers 601 and 602, respectively, bonded (e.g., by ultrasonic welding or heat-sealing) along peripheral bond 633 and enclosing valve reed 650 as well as optional filtration material (not shown). In some embodiments, lower film layer 602 can optionally be part of the dressing construction (e.g., a portion of backing 110). Otherwise the valve 600 is sealed to the dressing using a thermal weld or an adhesive taking care to allow the exit port 660 communicate with the interior of the dressing. Optionally, filter elements may be placed in the antechamber or wound chamber to filter the medicament as it passes through the valve into the dressing.

Valve reed 650 comprises two valve reed film layers 651 and 652. Valve reed film layer 651 is bonded to upper film layer 601 along bond 690, and valve reed film layer 652 is bonded to lower film layer 602 along bond 691. Valve inlet 640 is not bonded shut. In this manner, two zones are created, inlet antechamber 630 and exit chamber 670 and the only way medicament may pass between antechamber 630 and exit chamber 670 is to pass through reed 650 at valve inlet 640. Inlet port 610 is defined in antechamber 630. Inlet port 610 may fit snugly to a pressurized container, however, it has been observed that if the volume flow of medicament is sufficient from the pressurized container then a snug fit is not necessary. The critical requirement is that the pressure generated must exceed the cracking pressure of the valve reed. Exit port 660 is provided in lower film 602 which will communicate with a backing of a medical dressing of the present disclosure.

Figure 8A:
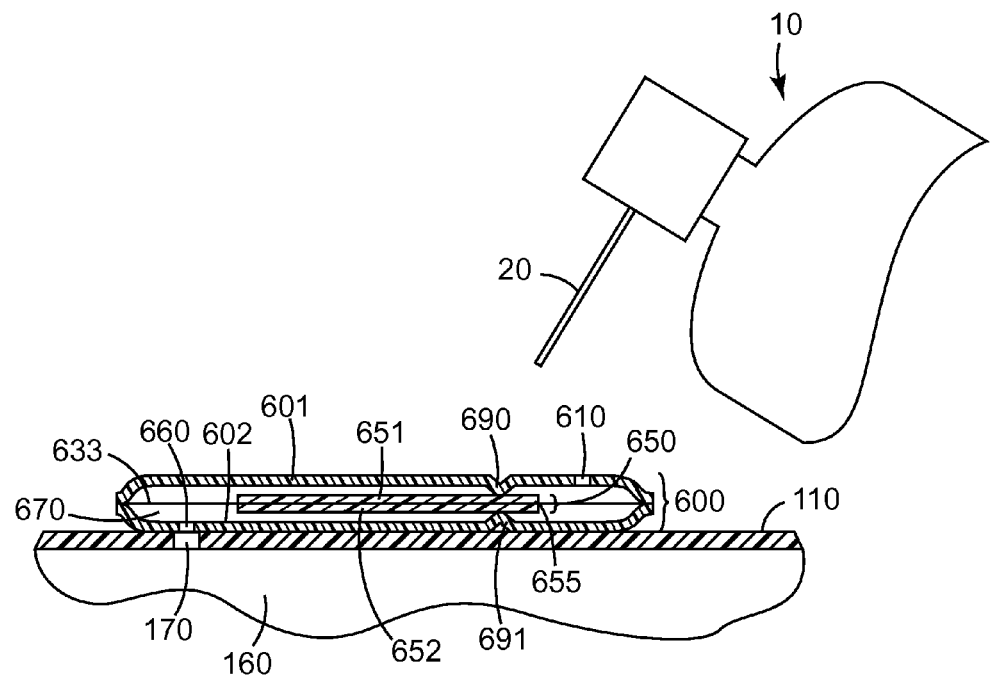
FIGS. 8A and 8B are schematic cross-sectional views of an exemplary embodiment of a normally-closed one-way flow control valve of the present disclosure.
Figure 8B:
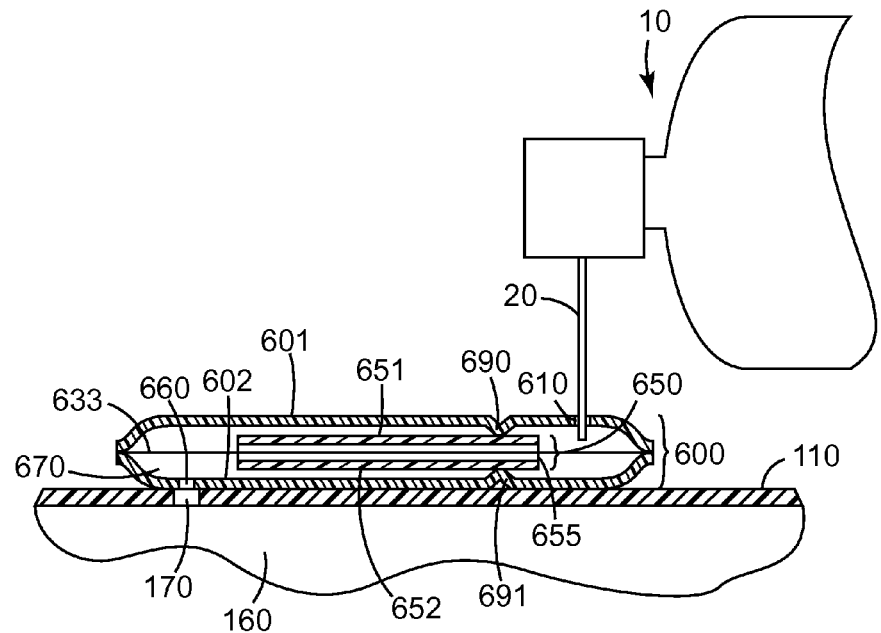

Shown in FIG. 8A is a cross-sectional view of normally-closed one-way flow control valve 600 affixed to backing 110. Valve reed 650 is shown with valve reed film layers 651 and 652 in contact with each other at valve reed passage 655 in a sealed condition. In FIG. 8B, valve reed film layers 651 and 652 are shown parted as would occur during instillation of the medicament from pressurized container 10 through straw 20 (i.e., valve reed passage 655 is "open"). Medicament must pass through valve reed 650 to get from the antechamber 630 to dressing side exit chamber 670. There is an inlet port 610 formed in upper film 601 and an exit port 660 in the dressing side film 602. If desired, film 602 may be an integral part of backing 110.

Antechambers may take on other forms. For example, when a flat film valve is used, the antechamber may simply be a tube (not shown) into which medicament delivery straw 20 is placed. The tube can optionally contain a filter element (not shown). Straw 20 may or may not form a seal with the antechamber so long as the pressure and volume are sufficient to open the valve and at least partially fill the chamber. If the cracking pressure of the valve is sufficiently low, the rapidly released pressurized medicament will open the valve and inflate the dressing.

Many medicaments may be delivered as a gas or aerosol. As used herein an aerosol refers to a gaseous suspension of fine solid particles or liquid droplets. A combination also is possible in which the gas phase is a medicament such as oxygen. Suitable gaseous medicaments include gaseous oxygen in concentrations of 21-100% in an inert or active carrier, as well as dilute concentrations of chlorine, bromine, ozone, nitric oxide, and the like. Diluents for the medicaments may be any suitable gas such as a noble gas (nitrogen, argon), helium, air, oxygen and the like. When oxygen is the medicament preferably it is presented at a concentration in the gas of greater than 30% w/w, more preferably greater than 50%, and even more preferably greater than 75% w/w. In one preferred embodiment the oxygen delivered is present at a concentration of greater than 90%, preferably greater than 95% and most preferably greater than 98% w/w. The concentration of these agents must be adjusted to give a therapeutic effect (e.g., antibacterial activity, improved wound healing). The concentration can be diluted in a suitable carrier gas such as an inert gas (e.g. nitrogen or argon). Combinations of medicaments also are possible (e.g., a combination of oxygen and nitric oxide, or a combination of oxygen and ozone).

Aerosol medicaments can be many and may include antimicrobial agents, an antiseptic, an antibiotic, an analgesic, a vitamin, a steroid, a growth factor, a hormone, a nutrient, or chemotactic agents. A list of other possible medicaments that may be delivered in an aerosol form include heparin, covalent heparin, or another thrombin inhibitor, hirudin, hirulog, argatroban, D-phenylalanyl-L-poly-L-arginyl chloromethyl ketone, or another antithrombogenic agent, or mixtures thereof; urokinase, streptokinase, a tissue plasminogen activator, or another thrombolytic agent, or mixtures thereof; a fibrinolytic agent; a vasospasm inhibitor; a calcium channel blocker, a nitrate, nitric oxide, a nitric oxide promoter or another vasodilator; an antimicrobial agent or antibiotic; analgesics such as aspirin, methyl salicylate, camphor, menthol, a lower alcohol such as ethanol or isopropanol; local anesthetics such as lidocaine, benzocaine, priolocane, mixtures of these such as EMLA and the like; ticlopidine, a glycoprotein IIb/IIIa inhibitor or another inhibitor of surface glycoprotein receptors, or another antiplatelet agent; colchicine or another antimitotic, or another microtubule inhibitor, dimethyl sulfoxide (DMSO), a retinoid or another antisecretory agent; cytochalasin or another actin inhibitor; or a remodeling inhibitor; deoxyribonucleic acid, an antisense nucleotide or another agent for molecular genetic intervention; methotrexate or another antimetabolite or antiproliferative agent; tamoxifen citrate, paclitaxel ("TAXOL") or derivatives thereof, or other anti-cancer chemotherapeutic agents; dexamethasone, dexamethasone sodium phosphate, dexamethasone acetate or another dexamethasone derivative, or another anti-inflammatory steroid or non-steroidal anti-inflammatory agent; cyclosporin or another immunosuppressive agent; trapidal (a PDGF antagonist), angiogenin, angiopeptin (a growth hormone antagonist), a growth factor or an anti-growth factor antibody, or another growth factor antagonist; dopamine, bromocriptine mesylate, pergolide mesylate or another dopamine agonist; iodine-containing compounds; a peptide, a protein, an enzyme, an extracellular matrix component, a cellular component or another biologic agent; captopril, enalapril or another angiotensin converting enzyme (ACE) inhibitor; ascorbic acid, alpha tocopherol, superoxide dismutase, deferoxamine, a 21-amino steroid (lasaroid) or another free radical scavenger, iron chelator or antioxidant; estrogen or another sex hormone; AZT or other antipolymerases; acyclovir, famciclovir, rimantadine hydrochloride, ganciclovir sodium or other antiviral agents; 5-aminolevulinic acid, meta-tetrahydroxyphenylchlorin, hexadecafluoro zinc phthalocyanine, tetramethyl hematoporphyrin, rhodamine 123 or other photodynamic therapy agents; an IgG2 Kappa antibody against *Pseudomonas aeruginosa* exotoxin A and reactive with A431 epidermoid carcinoma cells, monoclonal antibody against the noradrenergic enzyme dopamine beta-hydroxylase conjugated to saporin or other antibody targeted therapy agents; gene therapy agents; and enalapril and other prodrugs, or a mixture of any of these. Examples of other potentially suitable agents may be described in U.S. Pat. No. 6,867,342.

Medical dressings of the present disclosure may be particularly suited for treating post operative surgical wounds. The medical dressings also may be suited for treating infected tissue and spaces such as abscesses, an infected peritoneal cavity (peritonitis), topical impetigo and the like. In this manner, the tissue is treated while containing the pathogenic organism. These applications may require a relatively small dressing for an abscess (e.g. less than 7.5 cm square) to very large dressings/drapes for applications such as peritonitis. Treatment of peritonitis may include performing a lavage with a liquid medicament such as an antibiotic solution, saline, hypertonic saline, an antiseptic solution etc. through the valve into the dressing with subsequent or simultaneous withdrawal of fluid through an exit valve. The exit valve is preferably a one way out valve such as those described in U.S. Published Patent Application No. 2011/0106030, which is incorporated by reference herein for this purpose. For large applications (e.g., treatment of peritonitis) it is also possible to take a small valve dressing the present disclosure and place it over a larger dressing or an adhesive coated drape (e.g., and incise drape such that available from 3M Company, Maplewood Minn., under the trade designation "IOBAN II") after making a small hole in the dressing or drape so that the dressing can communicate with the tissue.

In certain applications the medicament may be colored to indicate to the clinician or user that the medicament has been delivered which can be visualized through a transparent dressing. Alternatively, the dressing or a dressing component could change color in response to the introduction of medicament. For example, the dressing could have one or more pH sensitive dyes that change color with the introduction of a medicament that alters the pH for example, by inclusion of carbon dioxide which will form carbonic acid.

If delivered, an active agent (or agents) could be supplied to the normally-sealed environment continuously or intermittently. For example, an active agent could be delivered to the normally-sealed environment and allowed to remain in place (i.e., resident) for a selected period of time (e.g., several hours) followed by delivery of a second active agent, or delivery of a combination of active agents. The initial active agent could be removed before delivery of the second agent or it could be allowed to remain in place. Alternatively, the normally-sealed environment could be rinsed (e.g., using air, saline or another flushing solution) before delivery of a second agent.

In some embodiments, a closure element may be attached to the exterior surface of the medical dressing over the valve, such that the valve is sealed shut by the closure element until the closure element is removed or otherwise opened. For the purposes of this disclosure the closure element is not included when considering the dead volume of the valve. The closure element can serve to help seal the valve or to protect it from becoming soiled. The closure element preferably is easy to disinfect with common disinfectants such as ethanol/water, isopropanol/water, n-propanol/water, hydrogen peroxide, iodine or other antiseptic composition. Most preferred closure elements prevent these antiseptic cleaning solutions from entering the valve where they could be forced into the wound space.

The closure element may be attached using adhesives, heat sealing, welding, or casting, although it may be preferred that the closure element be attached using a pressure sensitive adhesive such that the closure element can be reattached to the medical dressing after it is removed from its location over the valve. In such an embodiment, the closure element may potentially be reattached to the medical dressing over the valve to reseal the valve and/or the closure element may be attached elsewhere on the medical dressing to seal an opening made through the backing (e.g., deliver materials into the normally-sealed environment as described herein).

The medicaments may be supplied sterile in addition to or in place of the filter elements described. Suitable sterilization methods include filter sterilization, ionizing radiation (e.g., gamma radiation, electron beam, or heat).

As mentioned previously, the medical dressing of the present disclosure may be useful as a topical or transdermal drug delivery device. In this embodiment the medical dressing is applied over the treatment site and the medicament is administered through the valve as previously described. Medicament administration can be performed one, two, three, or many times. The medicament may be administered as often as necessary without the need to remove the dressing. Dressing removal can cause significant skin stripping and irritation so a refillable rather than replaceable dressing can be particularly advantageous for the patient.

Backings:

The medical dressings of the present disclosure are useful in connection with any conformable backing that provides a sufficiently impermeable barrier to the passage of liquids and at least some gases. Representative backings may include polymeric films and other familiar backing materials. The preferred backing materials may be translucent or transparent polymeric films.

The backings used in connection with the present disclosure may be high moisture vapor permeable film backings. Issued U.S. Pat. Nos. 3,645,835 and 4,595,001 describe methods of making such films and methods for testing their permeability. The film (and any adhesive used thereon as described herein) may transmit moisture vapor at a rate equal to or greater than human skin. In some embodiments, the adhesive-coated film may transmit moisture vapor at a rate of at least 300 g/m$^2$/24 hrs/37° C./100-10% RH, more preferably at least 700 g/m$^2$/24 hrs/37° C./100-10% RH, and most preferably at least 2000 g/m$^2$/24 hrs/37° C./100-10% RH using the inverted cup method as described in U.S. Pat. No. 4,595,001.

The backings may also preferably be conformable to anatomical surfaces. As such, when the backing is applied to an anatomical surface, it conforms to the surface even when the surface is moved. The backing may also be conformable to animal anatomical joints. When the joint is flexed and then returned to its unflexed position, the backing may stretch to accommodate the flexion of the joint, but is resilient enough to continue to conform to the joint when the joint is returned to its unflexed condition. A description of this characteristic of backings can be found in issued U.S. Pat. Nos. 5,088,483 and 5,160,315. The backings should be sufficiently conformable to form a circumferential seal around the treatment area such as a wound. Examples of some potentially suitable backings may include elastomeric polyurethane, polyester, or polyether block amide films. These films combine the desirable properties of resiliency, high moisture vapor permeability, and transparency.

Commercially available examples of potentially suitable backing materials may include the thin polymeric film backings sold under the tradenames TEGADERM (3M Company), BIOSITE (Johnson & Johnson Company), OPSITE (Smith & Nephew). Many other backings may also be used, including those commonly used in the manufacture of surgical incise drapes (e.g., incise drapes manufactured by 3M Company under the tradename STERIDRAPE and IOBAN).

Because fluids may be actively removed from the normally-sealed environments defined by the medical dressings of the present disclosure, a relatively high moisture vapor permeable backing may not be required. As a result, some other potentially useful backing materials may include metallocene polyolefins and SBS and SIS block copolymer (e.g., KRATON type) materials could be used.

Regardless, however, it may be preferred that the backings be kept relatively thin (e.g., to improve conformability). For example, it may be preferred that the backings be formed of (e.g., consist essentially of) polymeric films with a thickness of 200 micrometers or less, or 100 micrometers or less, potentially 50 micrometers or less, or even 25 micrometers or less.

Pressure Sensitive Adhesives:

The pressure sensitive adhesives that may preferably be used in the medical dressings of the present disclosure may include adhesives that are typically applied to the skin such as the acrylate copolymers described in U.S. Pat. No. RE 24,906, particularly a 96:4 iso-octyl acrylate:acrylamide copolymer. Another example may include a 70:15:15 isooctyl acrylate:ethyleneoxide acrylate:acrylic acid terpolymer, as described in U.S. Pat. No. 4,737,410 (Example 31). Other potentially useful adhesives are described in U.S. Pat. Nos. 3,389,827; 4,112,213; 4,310,509; and 4,323,557. Inclusion of medicaments or antimicrobial agents in the adhesive is also contemplated, as described in U.S. Pat. Nos. 4,310,509 and 4,323,557.

The pressure sensitive adhesives may, in some embodiments, transmit moisture vapor at a rate greater to or equal to that of human skin. While such a characteristic can be achieved through the selection of an appropriate adhesive, it is also contemplated in the present disclosure that other methods of achieving a high relative rate of moisture vapor transmission may be used, such as pattern coating the adhesive on the backing, as described in U.S. Pat. No. 4,595,001. Other potentially suitable pressure sensitive adhesives may include blown-micro-fiber (BMF) adhesives such as, for example, those described in U.S. Pat. No. 6,994,904. The pressure sensitive adhesive used in the medical dressing may also include one or more areas in which the adhesive itself includes structures such as the microreplicated structures described in U.S. Pat. No. 6,893,655. Also useful are silicone based pressure sensitive adhesives such as those described in International (PCT) Published Patent Nos. WO2010/056544 and WO2013/022913, as well as those silicone adhesives described in International (PCT) Published Patent No. WO2013/025955.

Release Liners:

Release liners may be supplied with the medical dressings of the present disclosure to protect the pressure sensitive adhesive used to attach the dressings to the patient and create the normally-sealed environment. Release liners that may be suitable for use in the medical dressing of the present disclosure can be made of supercalendered kraft paper, glassine paper, polyethylene, polypropylene, polyester or composites of any of these materials. The liners are preferably coated with release agents such as fluorochemicals or silicones. For example, U.S. Pat. No. 4,472,480 describes low surface energy perfluorochemical liners. The liners may preferably be in the form of papers, polyolefin films, polyolefin coated paper or polyester films coated with silicone release materials. Examples of commercially available silicone coated release liners are POLY SLIK™ silicone release on polyolefin coated papers, FL2000™ silicone release on film, and STICK-NOT™ silicone release on supercalendered kraft paper, all available from Loparex Inc., (Willowbrook, Ill.); silicone coated supercalendered kraft paper from Akrosil, (Menasha, Wis.); and silicone release film from Huhtamaki Florchheim, (Florchheim, Germany). Another potential liner is silicone coated (1630) low density polyethylene available from Huhtamaki.

The selection of a specific release liner may be made in conjunction with the selection of a pressure sensitive adhesive. Those skilled in the art will be familiar with the processes of testing a new adhesive against different liners or a new liner against different adhesives to arrive at the combination of qualities desired in a final product. The considerations pertinent to the selection of a silicone release liner can be found in Chapter 18 of the *Handbook of Pressure Sensitive Adhesive Technology*, Van Nostrand-Reinhold, 1982, pp. 384-403. U.S. Pat. No. 4,472,480 also describes considerations pertinent to the selection of a perfluoropolyether release liner.

Carriers/Delivery Systems:

In some instances, the backings used in the medical dressings of the present disclosure may be so flexible and supple such that when a release liner is removed from the backing, the backing may tend to fold and adhere to itself, interfering with the smooth, aseptic application of the dressing to a patient's skin.

Figure 9:
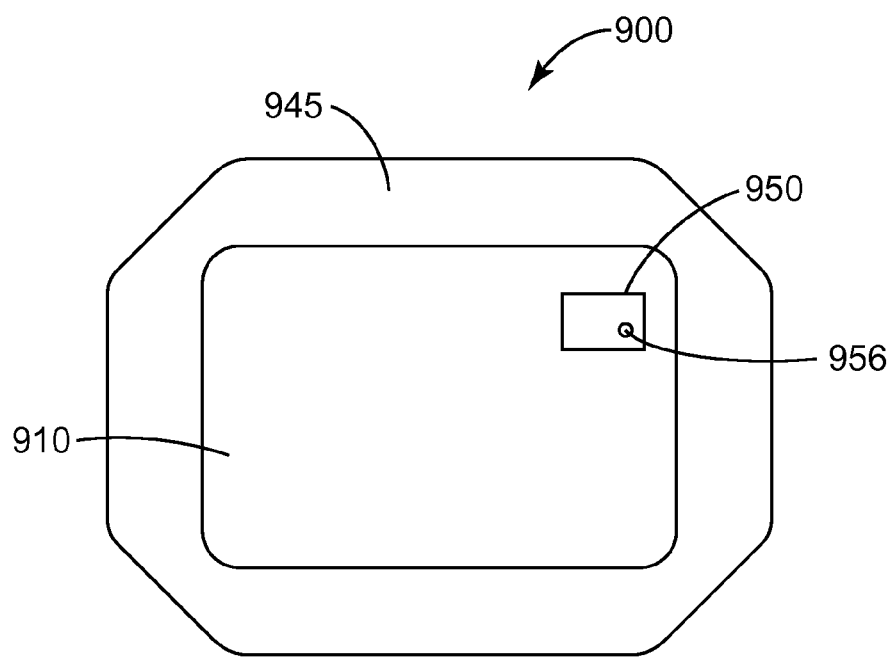
FIG. 9 is a schematic plan view of an exemplary embodiment of a medical dressing of the present disclosure.

Various delivery systems have been proposed to address this problem such as those disclosed in U.S. Pat. No. 4,485,809; U.S. Pat. No. 4,600,001; and EPO Publication No. 0 051 935. Carrier-type delivery systems such as those described in U.S. Pat. No. 6,685,682 offer an alternative delivery system for use with conformable backings. In these embodiments the carrier is attached to the top surface of the dressing (surface facing away from the skin). The carrier is used to facilitate placement of the dressing once the liner is removed. After application the carrier is removed. In the exemplary embodiment illustrated in FIG. 9, medical dressing 900 includes backing 910, normally-closed one way valve 950 having inlet port 956, and carrier element 945. Carrier element 945 can facilitate placement of a medical dressing of the present disclosure over a treatment site.

Alternative carriers and/or delivery systems may include frames, handles, and stiffening strips, as disclosed in U.S. Pat. Nos. 6,742,522; 5,979,450; 6,169,224; 5,088,483; 4,598,004; and D 493,230. Still another potentially suitable delivery system may be described in U.S. Patent Application Publication No. 2007/0156075 A1. In some instances, the backings can be delivered linerless (e.g., as described in U.S. Pat. No. 5,803,086).

Also included in the present disclosure are kits comprising a pressurized medicament container capable of filling the treatment dressing at least once, a treatment dressing as described herein comprising a normally closed flow control valve and optionally absorbent, border/carrier, rate controlling film or membrane and various other options described herein, and a means for temporarily connecting the pressurized medicament container to the treatment dressing and inflating the dressing. The pressurized medicament container may be filled to a suitable pressure as supplied to inflate the treatment dressing. The extent of inflation must be controlled (i.e. the inflation pressure must be limited to avoid having the dressing lift away from the treatment site and to prevent doing damage to a wound site). In applications over wounds the pressure should not be too high that the dressing distends into the wound and places pressure on the wound bed which could cut off blood flow. If the pressure in the medicament container is higher than the desired maximum inflation pressure the kits may optionally include a regulator either as a part of the medicament container, the dressing, the connection means or as a separate item in the flow path from the pressurized medicament container to the treatment site. The regulator serves to reduce the pressure of the delivered medicament to a pressure that will not result in dressing lift or wound damage. For example, the medicament container may be pressurized to 5 psig, 10 psig, 15 psig or more but a pressure of no more than 100 mmHg greater than atmospheric pressure is desired in the dressing at the treatment site. The regulator reduces the pressure delivered to 100 mmHg greater than atmospheric pressure to avoid problems. The dressings of the present disclosure may be provided sterile in a sealed package comprising one or more dressings. The dressings and package may be sterilized by any suitable method including gamma radiation, electron beam radiation, and ethylene oxide.

In some embodiments, the medical dressing having the normally-closed one-way flow control valve can be connected to a fluid metering system for administration of the medicament. In some embodiments, the fluid metering system can administer multiple doses of the medicament on a predetermined schedule into the medical dressing via the normally-closed one-way flow control valve. In some further embodiments, the fluid metering system can administer various concentrations and/or various combinations of medicament(s) (e.g., a steroidal medicament plus an antimicrobial medicament) on a predetermined schedule into the medical dressing via the normally-closed one-way flow control valve. In some further embodiments, the fluid metering system can also remove fluid from the medical dressing through a normally-closed one way outlet valve.

EMBODIMENTS

Item 1. A medical dressing comprising:

a backing having generally opposed first and second major surfaces, a passage defined therethrough connecting the first and second major surfaces, and a perimeter of the second major surface;

adhesive disposed at least proximate to the perimeter of the second major surface; and a normally-closed one-way flow control valve affixed to the backing and surrounding the passage therethrough;

wherein the normally-closed one-way flow control valve permits fluid flow in a first direction from the first major surface to the second major surface when in an open configuration and restricts fluid from flowing in a second direction from the second major surface to the first major surface when in a closed configuration; and wherein, if the medical dressing is applied over a treatment site, then the medical dressing defines a normally-sealed environment over the treatment site.

Item 2. The medical dressing of item 1, wherein a dead volume between the normally-closed one-way flow control valve and the backing is 10 mm$^3$ or less.

Item 3. The medical dressing of any preceding item, wherein the normally-closed one-way flow control valve comprises an antechamber defining an external opening, and wherein administration of a pressurized fluid through the external opening opens the normally-closed one-way flow control valve.

Item 4. The medical dressing of any preceding item, wherein application of a positive pressure to an exterior surface of the normally-closed one-way flow control valve opens the normally-closed valve such that fluid within a pressurized medicament container can enter the normally-sealed environment.

Item 5. The medical dressing of any preceding item, wherein the normally-closed one-way flow control valve is flexible and may be easily folded in at least one direction between the thumb and forefinger of a healthcare worker.

Item 6. The medical dressing of any preceding item, further comprising a closure element attached to the first major surface of the backing and covering the normally-closed one-way flow control valve, wherein the closure element seals the normally-closed one-way flow control valve shut.

Item 7. The medical dressing of any preceding item, further comprising a fitting adapted for attachment to the first major surface of the backing over the normally-closed one-way flow control valve.

Item 8. The medical dressing of any preceding item, further comprising a barrier element attached proximate to the second major surface of the backing.

Item 9. The medical dressing of any preceding item, further comprising a septum element attached to the backing.

Item 10. The medical dressing of any preceding item, wherein the normally-closed one-way flow control valve is constructed of thin films.

Item 11. The medical dressing of any preceding item, wherein the normally-closed one-way flow control valve is constructed to provide a flattened channel which opens upon pressurization with a pressurized medicament.

Item 12. A medical dressing kit, the kit comprising:
 a medical dressing according to any of items 1 to 5;
 optionally, a closure element;
 optionally, a barrier element;
 optionally, wound fluid absorbent material;
 optionally, a rate control film/membrane
 optionally, a medicament reservoir;
 optionally, a fitting adapted for attachment to the external surface of the backing over the normally-closed one-way flow control valve; and
 optionally, one or more containers of pressurized medicament
  optionally a connection means
  optionally a pressure regulator.

Item 13. A medical dressing kit according to item 12, wherein the closure element is pre-attached to the backing.

Item 14. A medical dressing kit according to item 12, wherein the closure element is not attached to the backing.

Item 15. A medical dressing kit according to item 12, having a closure element attached to the first major surface of the backing over the normally-closed one-way flow control valve, wherein the closure element seals the normally-closed one-way flow control valve shut.

Item 16. A method of treating a wound, the method comprising:
 applying a medical dressing according to any one of items 1 to 11 over a wound;
 introducing a pressurized fluid medicament into the normally-sealed environment through the valved opening in the backing.

Item 17. A method according to item 16, wherein the fluid medicament introduced into the normally-sealed environment comprises a gas such that the pressure within the normally-sealed environment is in a range of from 0.1 mmHg up to 100 mmHg for a period of at least one minute.

Item 18. A method according to item 16, wherein the fluid medicament introduced into the normally-sealed environment comprises an oxygen concentration in a range from 21% up to 100%.

Item 19. A method according to item 16, wherein the fluid medicament introduced into the normally-sealed environment comprises one of a nitric oxide, ozone, iodine or hydrogen peroxide.

The complete disclosure of the patents, patent documents, and publications cited herein are incorporated by reference in their entirety as if each were individually incorporated (although conflicts between any such disclosures and the descriptions explicitly provided herein should be resolved in favor of this document).

Exemplary embodiments of this invention are discussed and reference has been made to possible variations within the scope of this disclosure. These and other variations and modifications in the disclosure will be apparent to those skilled in the art without departing from the scope of the disclosure, and it should be understood that this disclosure is not limited to the exemplary embodiments set forth herein. Accordingly, the invention is to be limited only by the claims provided below and equivalents thereof.

What is claimed is:

1. A medical dressing comprising:
 a backing having generally opposed first and second major surfaces, a passage defined therethrough connecting the first and second major surfaces, and a perimeter of the second major surface;
 adhesive disposed at least proximate to the perimeter of the second major surface; and
 a normally-closed one-way flow control valve affixed to the backing and surrounding the passage therethrough;
 wherein the normally-closed one-way flow control valve comprises a valve reed that defines a portion of the passage;
 wherein the normally-closed one-way flow control valve permits fluid flow in a first direction from the first major surface to the second major surface when in an open configuration and restricts fluid from flowing in a second direction from the second major surface to the first major surface when in a closed configuration; and
 wherein, if the medical dressing is applied over a treatment site, then the medical dressing defines a normally-sealed environment over the treatment site;
 wherein the normally-closed one-way flow control valve comprises an antechamber defining an external opening, and wherein administration of a pressurized fluid through the external opening opens the normally-closed one-way flow control valve.

2. The medical dressing of claim 1, wherein a dead volume between the normally-closed one-way flow control valve and the backing is 10 mm$^3$ or less.

3. The medical dressing of claim 1, wherein application of a positive pressure to an exterior surface of the normally-closed one-way flow control valve opens the normally-closed valve such that fluid within a pressurized medicament container can enter the normally-sealed environment.

4. The medical dressing of claim 1, wherein the normally-closed one-way flow control valve is flexible and may be easily folded in at least one direction between the thumb and forefinger of a healthcare worker.

5. The medical dressing of claim 1, further comprising a closure element attached to the first major surface of the backing and covering the normally-closed one-way flow control valve, wherein the closure element seals the normally-closed one-way flow control valve shut.

6. The medical dressing of claim 1, further comprising an inlet port adapted for attachment to the first major surface of the backing over the normally-closed one-way flow control valve.

7. The medical dressing according to claim 1, wherein the backing has a moisture vapor transmission rate of at least 300 g/m$^2$/24 hrs/37° C./100-10% RH.

8. The medical dressing of claim 1, wherein the valve reed comprises a first layer and a second layer, wherein the first layer contacts the second layer in the closed configuration and is parted in an open configuration.

9. The medical dressing of claim 3, wherein the positive pressure is higher than a cracking pressure of the valve reed.

10. The medical dressing of claim 1, wherein the valve reed is bonded to the backing.

11. The medical dressing of claim 10, wherein the valve reed is bonded to the backing using transverse bonds.

12. A medical dressing kit, the kit comprising:

a medical dressing according to claim 1;

a closure element attached to the first major surface of the backing over the normally-closed one-way flow control valve, wherein the closure element seals the normally-closed one-way flow control valve shut.

13. The medical dressing kit according to claim 12, further comprising at least one of: a wound fluid absorbent material, a medicament reservoir, and combinations thereof.

14. The medical dressing kit according to claim 12, further comprising at least one of: a pressurized medicament container, connection means to interface the pressurized medicament container with the normally-closed one-way flow control valve, and combinations thereof.

15. A method of treating a wound, the method comprising:
applying a medical dressing according to claim 1 over a wound;
introducing a pressurized fluid medicament into the normally-sealed environment through the valved opening in the backing.

16. A method according to claim 15, wherein the fluid medicament introduced into the normally-sealed environment comprises a gas such that the pressure within the normally-sealed environment is in a range of from 0.1 mmHg up to 100 mm Hg for a period of at least one minute.

17. A method according to claim 15, wherein the fluid medicament introduced into the normally-sealed environment comprises an oxygen concentration in a range from 21% up to 100%.

18. A method according to claim 15, wherein the fluid medicament introduced into the normally-sealed environment comprises one of a nitric oxide, ozone, iodine or hydrogen peroxide.

* * * * *